United States Patent [19]

Seele et al.

[11] Patent Number: 5,204,362
[45] Date of Patent: Apr. 20, 1993

[54] FUNGICIDAL AZOLYLETHANE DERIVATIVES

[75] Inventors: Rainer Seele, Fussgoenheim; Norbert Goetz, Worms; Wolfgang Brox, Heidelberg; Reiner Kober, Fussgoenheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 675,170

[22] Filed: Mar. 26, 1991

[30] Foreign Application Priority Data

Mar. 26, 1990 [DE] Fed. Rep. of Germany ....... 4009594

[51] Int. Cl.[5] ................. A01N 43/653; C07D 405/06; C07D 409/06
[52] U.S. Cl. .................... 514/383; 514/184; 548/101; 548/266.6
[58] Field of Search ............ 548/101, 266.6; 514/184, 383

[56] References Cited

U.S. PATENT DOCUMENTS

| | | | |
|---|---|---|---|
| 4,102,891 | 7/1978 | Timmler et al. | 548/262.2 |
| 4,315,016 | 2/1982 | Balassabramanyan et al. | 514/383 |
| 4,394,380 | 7/1983 | Balassabramanyan et al. | 514/383 |
| 4,411,687 | 10/1983 | Zeeh et al. | |

FOREIGN PATENT DOCUMENTS 0091219 10/1983 European Pat. Off. .

*Primary Examiner*—Patricia L. Morris
*Attorney, Agent, or Firm*—Oblon, Spivak, McClelland, Maier & Neustadt

[57] ABSTRACT

Azolylethane derivatives of the formula I

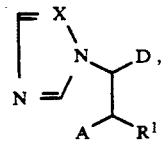

where
A and $R^1$ are each alkyl, phenyl, biphenyl, naphthyl, benzyl, cycloalkyl, alkoxy, alkylthio, phenoxy, benzyloxy, phenylthio, methoxycarbonylethyl or hetaryl, these radicals being substituted or unsubstituted,
D is halogen, alkoxy, alkylthio, phenylthio or phenoxy, these radicals being substituted or unsubstituted,
X is CH or N,
plant-tolerated acid addition salts and metal complex compounds thereof, and fungicides containing these compounds.

6 Claims, No Drawings

FUNGICIDAL AZOLYLETHANE DERIVATIVES

The present invention relates to novel useful azolylethane derivatives having a fungicidal action, fungicides containing these derivatives and methods for controlling fungi with these compounds.

It is known that azolylethane derivatives, e.g. 1-(1,2,4-triazol-1-yl)-1-phenylthio-2-methyl-2-phenylpropane or 1-(1,2,4-triazol-1-yl)-1-(4-chlorophenylthio)-2-methyl-2-phenylpropane (EP 91 219) or 1-methoxy-1-(1,2,4-triazol-1-yl)-2-phenylethane (DE 26 40 823), can be used as fungicides. However, their action is unsatisfactory.

It is an object of the present invention to provide novel compounds having improved biological activity.

We have found that novel azolylethane derivatives of the general formula I

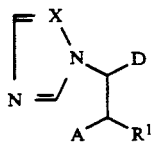

where

A and $R^1$ are identical or different and are each $C_1$–$C_8$-alkyl, phenyl, biphenyl, naphthyl, benzyl, $C_3$–$C_6$-cyclo-alkyl, $C_1$–$C_8$-alkoxy, $C_1$–$C_8$-alkylthio, phenoxy, benzyloxy, phenylthio, methoxycarbonylethyl or 5-membered or 6-membered hetaryl, and these radicals may be monosubstituted to trisubstituted by halogen, nitro, phenoxy, $C_1$–$C_4$-alkyl, $C_1$–$C_4$-alkoxy or $C_1$–$C_4$-haloalkyl, with the proviso that one or both of the substituents A and B is or are $C_1$–$C_8$-alkoxy, $C_1$–$C_8$-alkylthio, phenoxy, benzyloxy, phenylthio or 5-membered or 6-membered hetaryl, D is halogen, $C_1$–$C_4$-alkoxy, $C_1$–$C_4$-alkylthio, phenylthio or phenoxy, and these radicals may be monosubstituted to trisubstituted by halogen, nitro, phenoxy, $C_1$–$C_4$-alkyl or $C_1$–$C_4$-haloalkyl, and X is CH or N, and their plant-tolerated acid addition salts and metal complexes have a better fungicidal action than known azole compounds.

The substituents in formula I have, for example, the following specific meanings: A and B independently of one another are each straight-chain or branched $C_1$–$C_8$-alkyl, in particular $C_1$–$C_4$-alkyl, such as methyl, ethyl, propyl, isopropyl, butyl, isobutyl, sec-butyl or tert-butyl, $C_3$–$C_6$-cycloalkyl, such as cyclopropyl, cyclopentyl or cyclohexyl, benzyl, phenyl, naphthyl, such as 1-naphthyl or 2-naphthyl, biphenyl, such as o-, m- or p-biphenyl, straight-chain or branched $C_1$–$C_8$-alkoxy, in particular $C_1$–$C_4$-alkoxy, such as methoxy, ethoxy, propoxy, isopropoxy, butoxy, isobutoxy or tert-butoxy, straight-chain or branched $C_1$–$C_8$-alkylthio, in particular $C_1$–$C_4$-alkylthio, such as methylthio, ethylthio, propylthio, isopropylthio, butylthio, isobutylthio or secbutylthio, benzyloxy, phenoxy, phenylthio, methoxycarbonylethyl or 5-membered or 6-membered hetaryl, such as pyrrolyl, pyrrol-2-yl, pyrrol-3-yl, furan-2-yl, thien-2-yl, thien-3-yl, pyrid-2-yl, pyrid-3-yl, pyrid-4-yl, 1,3-diazol-2-yl, oxazol-4-yl, oxazol-5-yl, isoxazolyl, isoxazol-3-yl, isoxazol-4-yl, isoxazol-5-yl, thiazol-4-yl, thiazol-5-yl, imidazol-4-yl or 1,3-dioxolan-2-yl.

The stated radicals may be monosubstituted to trisubstituted by halogen, such as fluorine, chlorine or bromine, nitro, phenoxy, $C_1$–$C_4$-alkyl as stated specifically above, $C_1$–$C_4$-haloalkyl having from 1 to 3 halogen atoms, such as fluorine, chlorine or bromine, e.g. trifluoromethyl, chloroethyl or bromobutyl. D is halogen, such as chlorine or bromine, straight-chain or branched $C_1$–$C_4$-alkoxy as stated specifically above, straight-chain or branched $C_1$–$C_4$-alkylthio, as stated specifically above, phenoxy or phenylthio.

The stated radicals may be monosubstituted to trisubstituted by halogen, such as fluorine, chlorine or bromine, nitro, phenoxy, $C_1$–$C_4$-alkyl, e.g. methyl or ethyl, $C_1$–$C_4$-alkoxy as stated specifically above or $C_1$–$C_4$-haloalkyl having from 1 to 3 halogen atoms, such as fluorine, chlorine or bromine, e.g. trifluoromethyl.

The compounds of the formula I contain asymmetric carbon atoms and can therefore occur as enantiomers and diastereomers. The invention relates both to the pure isomers and to mixtures thereof. The mixtures of diastereomers can be separated into the components by known methods, for example by fractional crystallization or by chromatography over silica gel. The racemates of the novel compounds can be separated by conventional methods, for example by salt formation with an optically active acid, separation of the diastereomeric salts and liberation of the enantiomers by means of a base.

The individual diastereomers and mixtures thereof can be used as fungicidal active ingredients.

Acid addition salts are, for example, the hydrochlorides, bromides, sulfates, nitrates, phosphates, oxalates or dodecylbenzenesulfonates. The activity of the salts is due to the cation, so that the anion is generally unimportant. The acid addition salts are prepared by reacting the azolylethane derivatives (I) with acids.

Metal complexes of the active ingredients I or of their salts can be formed with, for example, copper, zinc, tin, manganese, iron, cobalt or nickel by reacting the azolylethane derivatives with metal salts.

The novel compounds I in which D is chlorine or bromine are very advantageously prepared, for example, similarly to the method described by H. Matsumoto et al. (Tetrahedron Lett. 52 (1979), 5011) by reacting an aldehyde of the formula II with an azole of the formula III and an acid halide (Y Hal$_2$) in accordance with the following empirical equation:

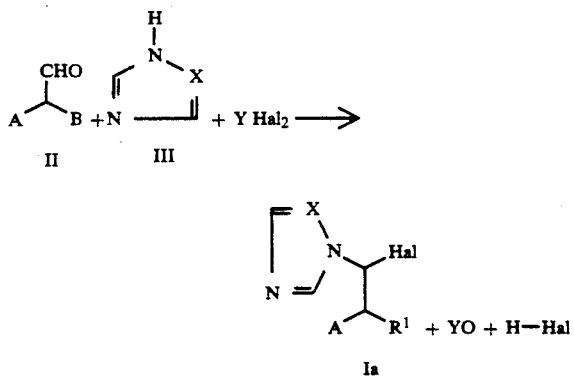

The inorganic acid halides (Y Hal$_2$) are halogenating agents, such as phosphorus oxychloride, thiophosgene, preferably phosgene, thionyl chloride and thionyl bromide.

The starting compounds II are known or are obtainable in a known manner (cf. H. Siegel, W. Himmele, Angew. Chem. 92 (1980), 182–187).

The acid halide is preferably used in not less than an equimolar amount, based on the aldehyde II. The azole component III is used, for example, in twice, preferably 5–6, times the molar amount, based on the acid chloride or bromide.

The reaction is preferably carried out at from $-30°$ to $+100°$ C., particularly preferably from $0°$ to $20°$ C., in the presence of a solvent.

Examples of preferred solvents are nitriles, such as acetonitrile and ethers, such as tetrahydrofuran, diethyl ether or dioxane. Hydrocarbons and chlorohydrocarbons, such as hexane, benzene, toluene, methylene chloride or carbon tetrachloride, or mixtures of the stated solvents are particularly preferred.

In general, the reaction is carried out at atmospheric pressure, unless a higher pressure, for example up to 5 bar, is advisable owing to readily volatile reactants.

Since the acid halides and the intermediates are sensitive to hydrolysis, the reaction is preferably carried out in the absence of moisture, particularly preferably in a protective gas atmosphere.

The novel compounds I in which D is $C_1$–$C_4$-alkoxy are very advantageously prepared, for example, similarly to the method described in DE 31 50 204, by reacting an acetal of the formula IV with an inorganic or organic acid chloride $R^1$-COCl and then with an azole of the formula III in accordance with the following empirical equation:

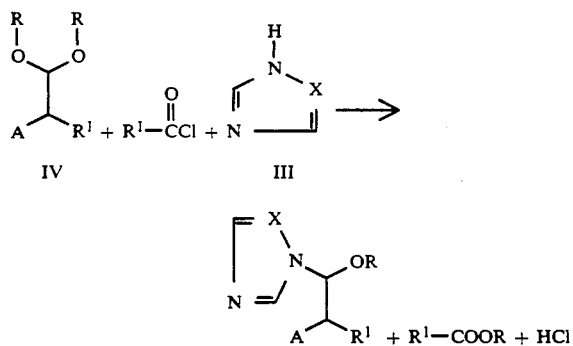

The starting compounds IV are known or are obtainable in a known manner by acetalization of the aldehydes II.

Suitable inorganic or organic acid halides are, for example, thionyl chloride, thionyl bromide, acetyl chloride and acetyl bromide. All conventional acid halides can also be used. The acid halide is preferably employed in an equimolar amount, based on the acetal IV. The azole component III is used in, for example, twice, preferably 4–6, times the molar amount, based on the acid halide.

The reaction is carried out at from $-30°$ to $+100°$ C., particularly preferably from $0°$ to $30°$ C., in the presence of a solvent.

Examples of preferred solvents are ketones, such as acetone, methyl ethyl ketone or cyclohexanone, nitriles, such as acetonitrile or propionitrile, alcohols, such as methanol, ethanol, isopropanol, n-butanol or glycols, esters, such as methyl acetate, ethyl acetate or butyl acetate, ethers, such as tetrahydrofuran, diethyl ether, dimethoxyethane, dioxane or diisopropyl ether, amides, such as dimethylformamide, dimethylacetamide or N-methylpyrrolidone, and dimethyl sulfoxide, sulfolane and mixtures of the stated solvents.

Since the acid halides and the intermediates are sensitive to hydrolysis, the reaction is preferably carried out in the absence of moisture, particularly preferably in a protective gas atmosphere.

The compounds I in which D is a substituent other than chlorine, bromine or $C_1$–$C_4$-alkoxy can be particularly advantageously prepared from the chlorine or bromine compounds Ia by reacting these with a compound H-D and a base.

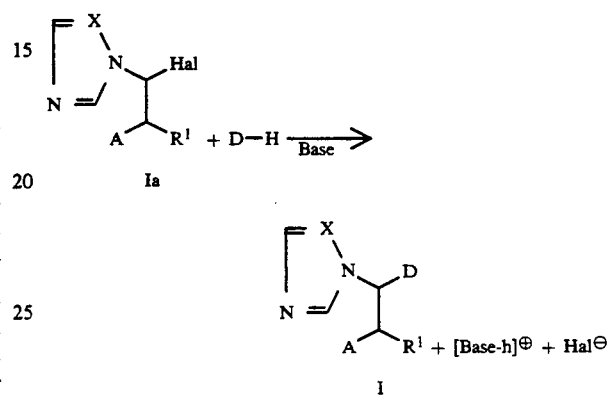

The component H-D is advantageously used in a stoichiometric amount, preferably in about 20% excess, based on the azolylethane derivative Ia.

The reaction is advantageously carried out with the addition of an organic or inorganic auxiliary base and/or of a reaction accelerator, in the presence of a solvent.

The amount of base and reaction accelerator may be varied depending on the compound used. Advantageously, a small excess of base, based on the azolylethane derivative Ia, is used.

Examples of suitable bases are alkali metal hydroxides, such as lithium hydroxide, sodium hydroxide or potassium hydroxide, alkali metal carbonates, such as sodium carbonate, potassium carbonate, sodium bicarbonate or potassium bicarbonate, alkali metal amides, such as sodium amide or potassium amide, and the organic bases pyridine, 4-dialkylaminopyridine, dialkylamines and dialkylanilines, or preferably the alkali metal salt of component H-D.

The reaction accelerator is preferably added to the reaction mixture in a catalytic amount.

Examples of suitable reaction accelerators are metal halides, preferably sodium iodide or potassium iodide, quaternary ammonium salts, such as tetraalkylammonium chloride, bromide or iodide, aryltrialkylammonium halides, such as benzyltriethylammonium chloride or bromide, and crown ethers, such as 12-crown-4, 15-crown-5, benzo-15-crown-5, dibenzo-18-crown-6 or dicyclohexano-18-crown-6.

Preferably used solvents are ketones, such as acetone, methyl ethyl ketone or cyclohexanone, nitriles, such as acetonitrile or propionitrile, alcohols, such as methanol, ethanol, isopropanol, n-butanol or glycols, esters, such as methyl acetate, ethyl acetate or butyl acetate, ethers, such as tetrahydrofuran, diethyl ether, dimethoxyethane, dioxane or diisopropyl ether, amides, such as dimethylformamide, dimethylacetamide or N-methylpyrrolidone, and dimethyl sulfoxide, sulfolane or mixtures of the stated solvents.

The reaction is advantageously carried out at from 0° to 180° C., preferably at the boiling point of the solvent used.

The novel process for the preparation of azolylethane derivatives can be carried out continuously or batchwise.

The Examples which follow illustrate the preparation of the active ingredients.

PREPARATION EXAMPLES

EXAMPLE 1

1-Chloro-1-(1,2,4-triazol-1-yl)-2-(4-methylphenoxy)-propane

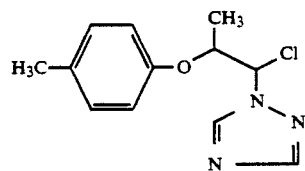

23.5 g (0.2 mol) of thionyl chloride were added to a solution of 54.5 g (0.79 mol) of triazole in 150 ml of methylene chloride at 0° C. under a nitrogen atmosphere, followed, after stirring for 30 minutes at 25° C., by 20 g of 2-(4-methylphenoxy)-propanal.

After a reaction time of 12 hours at 25° C., 100 ml of water were added, after which the aqueous phase was separated off and extracted twice with methylene chloride. The combined organic phases were then worked up in a conventional manner to obtain the triazole derivative.

Yield 25.5 g (84%).

EXAMPLE 2

1-Phenylthio-1-(1,2,4-triazol-1-yl)-2-(4-methylphenoxy)-propane

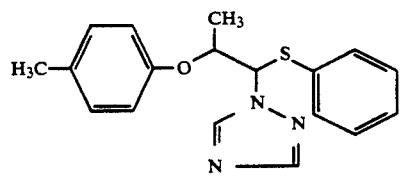

13 q (0.12 mol of thiophenol were added slowly at 25° C. to a solution of 4.0 g of sodium hydride (80% strength by weight suspension in mineral oil) and 100 ml of N,N-dimethylformamide, followed, after stirring for 30 minutes, by 19.8 g (0.08 mol) of 1-chloro-1-(1,2,4-triazol-1-yl)-2-(4-methylphenoxy)-propane. After a reaction time of 24 hours at 25° C., 100 ml of water were added. Extraction with methyl tert-butyl ether was carried out, after which the organic phase was washed and was worked up in a conventional manner.

Yield: 18.7 g (72%).

The compounds shown in the Table were prepared similarly to Examples 1 and 2.

TABLE

Structure:

$$\text{triazole-N}-\overset{D}{\underset{A\quad R^1}{CH-CH}}$$

| Example | A | $R^1$ | D | X | m.p./IR[cm$^{-1}$] | Isomer |
|---|---|---|---|---|---|---|
| 1 | CH$_3$ | O-(4-methylphenyl) | Cl | N | 1509, 1276, 1232, 1135, 815 | D$_1$:D$_2$ = 2:1 |
| 2 | CH$_3$ | O-(4-methylphenyl) | S-phenyl | N | resin | D$_1$:D$_2$ = 2:1 |
| 3 | CH$_3$ | O-phenyl | Cl | N | | |
| 4 | CH$_3$ | O-phenyl | Br | N | | |
| 5 | CH$_3$ | O-phenyl | O-(4-chlorophenyl) | N | | |

TABLE -continued

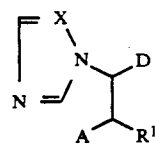

| Example | A | R¹ | D | X | m.p./IR[cm⁻¹] | Isomer |
|---|---|---|---|---|---|---|
| 6 | CH₃ | (phenoxy) | OCH₃ | N | | |
| 7 | CH₃ | (phenoxy) | OC₂H₅ | N | | |
| 8 | CH₃ | (phenoxy) | SCH₃ | N | | |
| 9 | CH₃ | (4-chlorophenoxy) | Cl | N | resin | D₁:D₂ = 2:1 |
| 10 | CH₃ | (4-chlorophenoxy) | OCH₃ | N | | |
| 11 | CH₃ | (4-chlorophenoxy) | OC₂H₅ | N | | |
| 12 | CH₃ | (4-chlorophenoxy) | (phenoxy) | N | resin | D₁:D₂ = 2:1 |
| 13 | CH₃ | (4-chlorophenoxy) | (4-chlorophenoxy) | N | | |
| 14 | CH₃ | (4-chlorophenoxy) | (4-chlorophenylthio) | N | | |
| 15 | CH₃ | (4-chlorophenoxy) | (phenylthio) | N | | |
| 16 | CH₃ | (2,4-dichlorophenoxy) | Cl | N | 1479, 1277, 1262, 1135, 802 | D₁:D₂ = 3:2 |

TABLE -continued

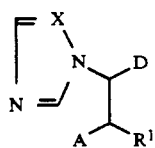

| Example | A | R¹ | D | X | m.p./IR[cm⁻¹] | Isomer |
|---|---|---|---|---|---|---|
| 17 | CH₃ | 2,4-dichlorophenoxy | OCH₃ | N | | |
| 18 | CH₃ | 2,4-dichlorophenoxy | OC₂H₅ | N | | |
| 19 | CH₃ | 2,4-dichlorophenoxy | phenylthio | N | | |
| 20 | CH₃ | 2,4-dichlorophenoxy | 4-chlorophenylthio | N | | |
| 21 | CH₃ | 2,4-dichlorophenoxy | phenoxy | N | | |
| 22 | CH₃ | 2,4-dichlorophenoxy | 4-chlorophenoxy | N | | |
| 23 | CH₃ | 2,4-dichlorophenoxy | 4-fluorophenylthio | N | | |
| 24 | CH₃ | 2,4-dichlorophenoxy | 2,4-dichlorophenoxy | N | | |
| 25 | CH₃ | 4-fluorophenoxy | Cl | N | | |
| 26 | CH₃ | 4-fluorophenoxy | OCH₃ | N | | |

TABLE -continued
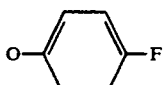
| Example | A | R¹ | D | X | m.p./IR[cm⁻¹] | Isomer |
|---|---|---|---|---|---|---|
| 27 | CH₃ | 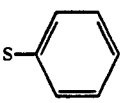 | 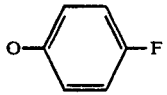 | N | | |
| 28 | CH₃ | 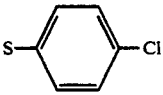 | 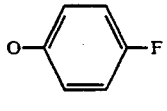 | N | | |
| 29 | CH₃ | 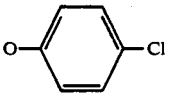 |  | N | | |
| 30 | CH₃ | 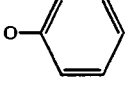 | 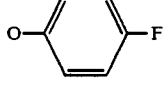 | N | | |
| 31 | CH₃ |  | 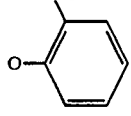 | N | | |
| 32 | CH₃ | 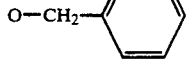 | Cl | N | resin | $D_1:D_2 = 3:1$ |
| 33 | CH₃ | 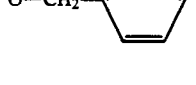 | Cl | N | 1505, 1276, 1136, 1100, 741, 698 | $D_1:D_2 = 6:5$ |
| 34 | CH₃ | 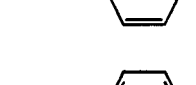 | OCH₃ | N | | |
| 35 | CH₃ | 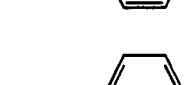 | OC₂H₅ | N | | |
| 36 | CH₃ | 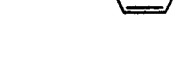 | SCH₃ | N | | |
| 37 | CH₃ | | | N | | |

TABLE -continued
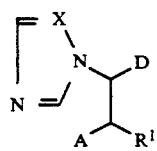
| Example | A | R¹ | D | X | m.p./IR[cm⁻¹] | Isomer |
|---|---|---|---|---|---|---|
| 38 | $CH_3$ | O—CH₂—C₆H₅ | S—C₆H₄—Cl (4-) | N | | |
| 39 | $CH_3$ | O—CH₂—C₆H₅ | O—C₆H₄—Cl (4-) | N | | |
| 40 | $CH_3$ | O—CH₂—C₆H₅ | O—C₆H₄—F (4-) | N | | |
| 41 | $CH_3$ | $OCH_3$ | Cl | N | | |
| 42 | $CH_3$ | $OCH_3$ | S—C₆H₅ | N | | |
| 43 | $CH_3$ | $OCH_3$ | S—C₆H₄—Cl (4-) | N | | |
| 44 | $CH_3$ | $OCH_3$ | O—C₆H₄—Cl (4-) | N | | |
| 45 | $CH_3$ | $OCH_3$ | O—C₆H₄—F (4-) | N | | |
| 46 | $CH_3$ | $OCH_3$ | O—C₆H₃—Cl₂ (2,4-) | N | | |
| 47 | $CH_3$ | $OC_2H_5$ | Cl | N | | |
| 48 | $CH_3$ | $O_2CH_5$ | S—C₆H₅ | N | | |
| 49 | $CH_3$ | $O_2CH_5$ | S—C₆H₄—Cl (4-) | N | | |
| 50 | $CH_3$ | $O_2CH_5$ | O—C₆H₄—Cl (4-) | N | | |

TABLE -continued

Structure header: molecule with N=, X, N, D substituent, and A-R¹ group.

| Example | A | R¹ | D | X | m.p./IR[cm⁻¹] | Isomer |
|---------|-----|--------|-----------------------------|---|---------------|--------|
| 51 | $CH_3$ | $O_2CH_5$ | 4-F-phenoxy (O-C₆H₄-F) | N | | |
| 52 | $CH_3$ | $OC_3H_7$ | Cl | N | | |
| 53 | $CH_3$ | $OC_3H_7$ | phenylthio (S-C₆H₅) | N | | |
| 54 | $CH_3$ | $OC_3H_7$ | 4-Cl-phenylthio (S-C₆H₄-Cl) | N | | |
| 55 | $CH_3$ | $OC_3H_7$ | 4-Cl-phenoxy (O-C₆H₄-Cl) | N | | |
| 56 | $CH_3$ | $OC_3H_7$ | 2,4-di-Cl-phenoxy | N | | |
| 57 | $CH_3$ | $OC_4H_9$ | Cl | N | | |
| 58 | $CH_3$ | $OC_4H_9$ | phenylthio (S-C₆H₅) | N | | |
| 59 | $CH_3$ | $OC_4H_9$ | 4-Cl-phenylthio (S-C₆H₄-Cl) | N | | |
| 60 | $CH_3$ | $OC_4H_9$ | 4-Cl-phenoxy (O-C₆H₄-Cl) | N | | |
| 61 | $CH_3$ | $OC_4H_9$ | 2,4-di-Cl-phenoxy | N | | |
| 62 | $CH_3$ | $S-CH_3$ | Cl | N | | |
| 63 | $CH_3$ | $S-CH_3$ | phenylthio (S-C₆H₅) | N | | |

TABLE -continued structure: ring-N=N-X with N-CH(D)-CH(A)(R¹)

| Example | A | R¹ | D | X | m.p./IR[cm⁻¹] | Isomer |
|---|---|---|---|---|---|---|
| 64 | CH₃ | S—CH₃ | 4-Cl-C₆H₄-S- | N | | |
| 65 | CH₃ | S—CH₃ | 4-Cl-C₆H₄-O- | N | | |
| 66 | CH₃ | S—C₂H₅ | Cl | N | | |
| 67 | CH₃ | S—C₂H₅ | C₆H₅-S- | N | | |
| 68 | CH₃ | S—C₂H₅ | 4-Cl-C₆H₄-S- | N | | |
| 69 | CH₃ | S—C₂H₅ | 4-Cl-C₆H₄-O- | N | | |
| 70 | CH₃ | C₆H₅-S- | Cl | N | | |
| 71 | CH₃ | C₆H₅-S- | 4-Cl-C₆H₄-S- | N | | |
| 72 | CH₃ | C₆H₅-S- | 4-Cl-C₆H₄-O- | N | | |
| 73 | CH₃ | C₆H₅-S- | 4-F-C₆H₄-O- | N | | |
| 74 | CH₃ | C₆H₅-S- | 2,4-Cl₂-C₆H₃-O- | N | | |
| 75 | H | C₆H₅ | Cl | N | | |
| 76 | H | 4-Cl—C₆H₄ | Cl | N | | |
| 77 | H | 2,4-Cl₂—C₆H₃ | Cl | N | | |
| 78 | H | 2-Cl—C₆H₄ | Cl | N | | |
| 79 | H | 4-F—C₆H₄ | Cl | N | resin | |

TABLE -continued structure: ring with X-N-D, N=, A, R¹ substituents

| Example | A | R¹ | D | X | m.p./IR[cm⁻¹] | Isomer |
|---|---|---|---|---|---|---|
| 80 | H | 4-F—C₆H₄ | S-C₆H₅ (phenylthio) | N | 1510, 1274, 1224, 1135, 748 | |
| 81 | H | 4-CH₃—C₆H₄ | Cl | N | | |
| 82 | H | 2-Thienyl | Cl | N | | |
| 83 | H | 3-Thienyl | Cl | N | | |
| 84 | H | 2-Furyl | Cl | N | | |
| 85 | C₂H₅ | O—C₆H₅ | Cl | N | | |
| 86 | C₂H₅ | O₃C₆H₅ | SC₆H₅ | N | | |
| 87 | C₂H₅ | O—C₆H₅ | S-C₆H₄-4-Cl | N | | |
| 88 | C₂H₅ | O-C₆H₄-4-CH₃ | Cl | N | | |
| 89 | C₂H₅ | O-C₆H₄-4-CH₃ | SC₆H₅ | N | | |
| 90 | C₂H₅ | O-C₆H₄-4-Cl | Cl | N | | |
| 91 | C₂H₅ | O-C₆H₄-4-Cl | SC₆H₅ | N | | |
| 92 | CH₃ | O-C₆H₄-4-Cl | O-C₆H₄-4-Cl | N | | |
| 93 | C₂H₅ | O-C₆H₃-2,4-Cl₂ | Cl | N | | |
| 94 | C₂H₅ | O-C₆H₃-2,4-Cl₂ | SC₆H₅ | N | | |

TABLE -continued

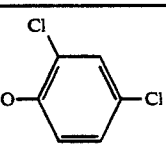

| Example | A | R¹ | D | X | m.p./IR[cm⁻¹] | Isomer |
|---|---|---|---|---|---|---|
| 95 | $C_2H_5$ | 2,4-di-Cl-C₆H₃-O- | 4-Cl-C₆H₄-O- | N | | |
| 96 | $C_2H_5$ | 2,4-di-Cl-C₆H₃-O- | 4-F-C₆H₄-O- | N | | |
| 97 | $C_2H_5$ | 4-F-C₆H₄-O- | Cl | N | | |
| 98 | $C_2H_5$ | 4-F-C₆H₄-O- | 4-Cl-C₆H₄-O- | N | | |
| 99 | $C_2H_5$ | 4-F-C₆H₄-O- | 2-Cl-C₆H₄-O- | N | | |
| 100 | $C_2H_5$ | 4-F-C₆H₄-O- | 4-F-C₆H₄-O- | N | | |
| 101 | $C_2H_5$ | $OCH_2-C_6H_5$ | Cl | N | | |
| 102 | $C_2H_5$ | $OCH_3$ | Cl | N | | |
| 103 | $C_2H_5$ | $OCH_3$ | 4-Cl-C₆H₄-O- | N | | |
| 104 | $C_2H_5$ | $OCH_3$ | 4-Cl-C₆H₄-S- | N | | |
| 105 | $C_2H_5$ | $OCH_3$ | $SC_6H_5$ | N | | |
| 106 | $C_2H_5$ | $OC_2H_5$ | Cl | N | | |
| 107 | $C_2H_5$ | $OC_3H_7$ | Cl | N | | |
| 108 | $C_2H_5$ | $SCH_3$ | Cl | N | | |
| 109 | $C_2H_5$ | $SC_2H_5$ | Cl | N | | |
| 110 | $C_2H_5$ | $SC_6H_5$ | Cl | N | | |
| 111 | $C_2H_5$ | $SC_6H_5$ | $OC_6H_5$ | N | | |
| 112 | $C_2H_5$ | $SC_6H_5$ | 4-Cl-C₆H₄-O- | N | | |

TABLE -continued structure: ring-N=X-N(-D)(-CH(A)(R^1)) with N=CH on ring

| Example | A | R¹ | D | X | m.p./IR[cm⁻¹] | Isomer |
|---|---|---|---|---|---|---|
| 113 | $C_2H_5$ | $SC_6H_5$ | O-C₆H₃(2-Cl,4-Cl) | N | | |
| 114 | $C_2H_5$ | $SC_6H_5$ | O-C₆H₄-4-F | N | | |
| 115 | $C_2H_5$ | $SC_6H_5$ | $SC_6H_5$ | N | | |
| 116 | $C_2H_5$ | $SC_6H_5$ | S-C₆H₄-4-Cl | N | | |
| 117 | $C_3H_7$ | $OC_6H_5$ | Cl | N | | |
| 118 | $C_3H_7$ | $OC_6H_5$ | $SC_6H_5$ | N | | |
| 119 | $C_3H_7$ | $OC_6H_5$ | S-C₆H₄-4-Cl | N | | |
| 120 | $C_3H_7$ | O-C₆H₄-4-CH₃ | Cl | N | | |
| 121 | $C_3H_7$ | O-C₆H₄-4-CH₃ | $SC_6H_5$ | N | | |
| 122 | $C_3H_7$ | O-C₆H₄-4-CH₃ | O-C₆H₄-4-Cl | N | | |
| 123 | $C_3H_7$ | O-C₆H₄-4-Cl | Cl | N | | |
| 124 | $C_3H_7$ | O-C₆H₄-4-Cl | $SC_6H_5$ | N | | |
| 125 | $C_3H_7$ | O-C₆H₄-4-Cl | O-C₆H₄-4-Cl | N | | |
| 126 | $C_3H_7$ | O-C₆H₃(2-Cl,4-Cl) | Cl | N | | |

TABLE -continued

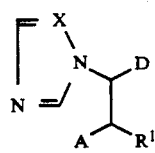

| Example | A | R¹ | D | X | m.p./IR[cm⁻¹] | Isomer |
|---|---|---|---|---|---|---|
| 127 | $C_3H_7$ | 2,4-dichlorophenoxy | 4-chlorophenoxy | N | | |
| 128 | $C_3H_7$ | 2,4-dichlorophenoxy | 4-fluorophenoxy | N | | |
| 129 | $C_3H_7$ | 4-fluorophenoxy | Cl | N | | |
| 130 | $C_3H_7$ | 4-fluorophenoxy | 2-chlorophenoxy | N | | |
| 121 | $C_3H_7$ | 4-fluorophenoxy | 4-fluorophenoxy | N | | |
| 132 | $C_3H_7$ | $OCH_2C_6H_5$ | Cl | N | | |
| 133 | $C_3H_7$ | $OCH_3$ | Cl | N | | |
| 134 | $C_3H_7$ | $OCH_3$ | 4-chlorophenoxy | N | | |
| 135 | $C_3H_7$ | $OCH_3$ | 4-chlorophenylthio | N | | |
| 136 | $C_3H_7$ | $OCH_3$ | $SC_6H_5$ | N | | |
| 137 | $C_3H_7$ | $OC_2H_5$ | Cl | N | | |
| 138 | $C_3H_7$ | $OC_3H_7$ | Cl | N | | |
| 139 | $C_3H_7$ | $SCH_3$ | Cl | N | | |
| 140 | $C_3H_7$ | $SC_2H_5$ | Cl | N | | |
| 141 | $C_3H_7$ | $SC_2H_5$ | $OC_6H_5$ | N | | |
| 142 | $C_3H_7$ | $SC_2H_5$ | 4-chlorophenoxy | N | | |
| 143 | $C_3H_7$ | $SC_2H_5$ | 2,4-dichlorophenoxy | N | | |

TABLE -continued
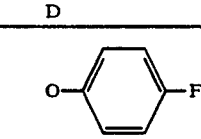
| Example | A | R¹ | D | X | m.p./IR[cm⁻¹] | Isomer |
|---|---|---|---|---|---|---|
| 144 | $C_3H_7$ | $SC_2H_5$ | 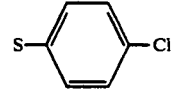 | N | | |
| 145 | $C_3H_7$ | $SC_2H_5$ | $SC_6H_5$ | N | | |
| 146 | $C_3H_7$ | $SC_2H_5$ | 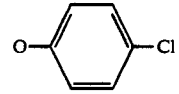 | N | | |
| 147 | $C_3H_7$ | $SC_6H_5$ | Cl | N | | |
| 148 | $C_3H_7$ | $SC_6H_5$ | $OC_6H_5$ | N | | |
| 149 | $C_3H_7$ | $SC_6H_5$ | 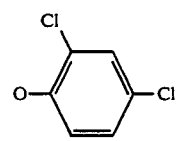 | N | | |
| 150 | $C_3H_7$ | $SC_6H_5$ | 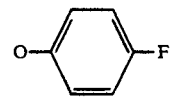 | N | | |
| 151 | $C_3H_7$ | $SC_6H_5$ | 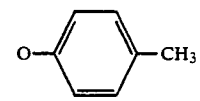 | N | | |
| 152 | $C_3H_7$ | $SC_6H_5$ | $SC_6H_5$ | N | | |
| 153 | $C_4H_9$ | $OC_6H_5$ | Cl | N | | |
| 154 | $C_4H_9$ | 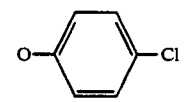 | Cl | N | | |
| 155 | $C_4H_9$ | 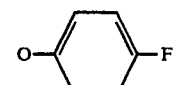 | Cl | N | | |
| 156 | $C_4H_9$ | 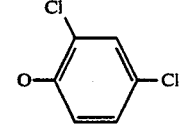 | Cl | N | | |
| 157 | $C_4H_9$ |  | Cl | N | | |
| 158 | $C_4H_9$ | $OCH_2C_6H_5$ | Cl | N | | |
| 159 | $C_4H_9$ | $OCH_3$ | Cl | N | | |
| 160 | $C_4H_9$ | $OC_3H_7$ | Cl | N | | |
| 161 | $C_4H_9$ | $SCH_3$ | Cl | N | | |
| 162 | $C_4H_9$ | $SC_6H_5$ | Cl | N | | |
| 163 | $C_6H_5$ | $OC_6H_5$ | Cl | N | | |

TABLE -continued

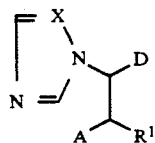

| Example | A | R¹ | D | X | m.p./IR[cm⁻¹] | Isomer |
|---|---|---|---|---|---|---|
| 164 | C₆H₅ | 4-CH₃-C₆H₄-O- | Cl | N | | |
| 165 | C₆H₅ | 4-Cl-C₆H₄-O- | Cl | N | | |
| 166 | C₆H₅ | 4-F-C₆H₄-O- | Cl | N | | |
| 167 | C₆H₅ | 2,4-Cl₂-C₆H₃-O- | Cl | N | | |
| 168 | C₆H₅ | OCH₃ | Cl | N | | |
| 169 | C₆H₅ | SCH₃ | Cl | N | | |
| 170 | C₆H₅ | SC₆H₅ | Cl | N | | |
| 171 | 4-F—C₆H₄ | OC₆H₅ | Cl | N | | |
| 172 | 4-F—C₆H₄ | 4-CH₃-C₆H₄-O- | Cl | N | | |
| 173 | 4-F—C₆H₄ | 4-Cl-C₆H₄-O- | Cl | N | | |
| 174 | 4-F—C₆H₄ | 4-F-C₆H₄-O- | Cl | N | | |
| 175 | 4-F—C₆H₄ | 2,4-Cl₂-C₆H₃-O- | Cl | N | | |
| 176 | 4-F—C₆H₄ | OCH₃ | Cl | N | | |
| 177 | 4-F—C₆H₄ | SCH₃ | Cl | N | | |
| 178 | 4-F—C₆H₄ | SC₆H₅ | Cl | N | | |
| 179 | 2-F—C₆H₄ | OC₆H₅ | Cl | N | | |
| 180 | 2-F—C₆H₄ | OCH₃ | Cl | N | | |
| 181 | 2-F—C₆H₄ | SC₆H₅ | Cl | N | | |
| 182 | 4-Cl—C₆H₄ | OC₆H₅ | Cl | N | | |
| 183 | 4-Cl—C₆H₄ | 4-CH₃-C₆H₄-O- | Cl | N | | |

TABLE -continued

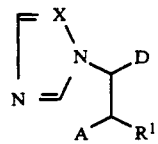

| Example | A | R¹ | D | X | m.p./IR[cm⁻¹] | Isomer |
|---|---|---|---|---|---|---|
| 184 | 4-Cl—C₆H₄ | -O-C₆H₄-4-Cl | Cl | N | | |
| 185 | 4-Cl—C₆H₄ | -O-C₆H₄-4-F | Cl | N | | |
| 186 | 4-Cl—C₆H₄ | -O-C₆H₃-2,4-Cl₂ | Cl | N | | |
| 187 | 4-Cl—C₆H₄ | OCH₃ | Cl | N | | |
| 188 | 4-Cl—C₆H₄ | SCH₃ | Cl | N | | |
| 189 | 4-Cl—C₆H₄ | SC₆H₅ | Cl | N | | |
| 190 | 2-Cl—C₆H₄ | OC₆H₅ | Cl | N | | |
| 191 | 2-Cl—C₆H₄ | OCH₃ | Cl | N | | |
| 192 | 2-Cl—C₆H₄ | SC₆H₅ | Cl | N | | |
| 193 | 2,4-Cl₂—C₆H₃ | OC₆H₅ | Cl | N | | |
| 194 | 2,4-Cl₂—C₆H₃ | OCH₃ | Cl | N | | |
| 195 | 2,4-Cl₂—C₆H₃ | SC₆H₅ | Cl | N | | |
| 196 | 4-Br—C₆H₄ | OCH₃ | Cl | N | | |
| 197 | 4-CH₃—C₆H₄ | OC₆H₅ | Cl | N | | |
| 198 | 4-CH₃—C₆H₄ | OCH₃ | Cl | N | | |
| 199 | 4-CH₃—C₆H₄ | SC₆H₅ | Cl | N | | |
| 200 | 4-OCH₃—C₆H₄ | OC₆H₅ | Cl | N | | |
| 201 | 4-OCH₃—C₆H₄ | OCH₃ | Cl | N | | |
| 202 | 4-OCH₃—C₆H₄ | SC₆H₅ | Cl | N | | |
| 203 | 4-CF₃—C₆H₄ | OC₆H₅ | Cl | N | | |
| 204 | 4-CF₃—C₆H₄ | OCH₃ | Cl | N | | |
| 205 | 4-CF₃—C₆H₄ | SC₆H₅ | Cl | N | | |
| 206 | 4-Biphenyl | OC₆H₅ | Cl | N | | |
| 207 | 4-Biphenyl | OCH₃ | Cl | N | | |
| 208 | 4-Biphenyl | SC₆H₅ | Cl | N | | |
| 209 | 1-Naphthyl | OCH₃ | Cl | N | | |
| 210 | 2-Naphthyl | OC₆H₅ | Cl | N | | |
| 211 | 2-Naphthyl | OCH₃ | Cl | N | | |
| 212 | 2-Naphthyl | SC₆H₅ | Cl | N | | |
| 213 | Cyclopentyl | OC₆H₅ | Cl | N | | |
| 214 | Cyclopentyl | -O-C₆H₃-2,4-Cl₂ | Cl | N | | |
| 215 | Cyclopentyl | OCH₃ | Cl | N | | |
| 216 | Cyclopentyl | SC₆H₅ | Cl | N | | |
| 217 | Cyclohexyl | OC₆H₅ | Cl | N | | |
| 218 | Cyclohexyl | -O-C₆H₃-2,4-Cl₂ | Cl | N | | |
| 219 | Cyclohexyl | OCH₃ | Cl | N | | |
| 220 | Cyclohexyl | SC₆H₅ | Cl | N | | |
| 221 | 2-Thienyl | CH₃ | Cl | N | | |

TABLE -continued

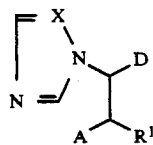

| Example | A | R¹ | D | X | m.p./IR[cm⁻¹] | Isomer |
|---|---|---|---|---|---|---|
| 222 | 2-Thienyl | CH₃ | —O—C₆H₄—Cl (4-) | N | | |
| 223 | 2-Thienyl | C₂H₅ | Cl | N | | |
| 224 | 2-Thienyl | C₂H₅ | —O—C₆H₄—Cl (4-) | N | | |
| 225 | 2-Thienyl | C₃H₇ | Cl | N | 2960, 1506, 1275, 1135, 701 | D₁:D₂ = 3:2 |
| 226 | 2-Thienyl | C₃H₇ | Cl | CH | 2959, 1489, 1226, 1078, 701 | D₁:D₂ = 2:1 |
| 227 | 2-Thienyl | C₃H₇ | OCH₃ | N | | |
| 228 | 2-Thienyl | C₃H₇ | —O—C₆H₄—Cl (4-) | N | | |
| 229 | 2-Thienyl | C₃H₇ | SC₆H₅ | N | | |
| 230 | 2-Thienyl | C₃H₇ | —S—C₆H₄—Cl (4-) | N | | |
| 231 | 2-Thienyl | C₆H₅ | Cl | N | | |
| 232 | 2-Thienyl | 4-Cl—C₆H₄ | Cl | N | | |
| 233 | 2-Thienyl | 2-Cl—C₆H₄ | Cl | N | | |
| 234 | 2-Thienyl | 2,4-Cl₂—C₆H₃ | Cl | N | | |
| 235 | 2-Thienyl | 4-F—C₆H₄ | Cl | N | | |
| 236 | 2-Thienyl | 4-CH₃—C₆H₄ | Cl | N | | |
| 237 | 2-Thienyl | 4-OCH₃—C₆H₄ | Cl | N | | |
| 238 | 2-Thienyl | 4-Biphenyl | Cl | N | | |
| 239 | 2-Thienyl | 1-Naphthyl | Cl | N | | |
| 240 | 2-Thienyl | 2-Naphthyl | Cl | N | | |
| 241 | 2-Thienyl | CH₂—C₆H₅ | Cl | N | | |
| 242 | 2-Thienyl | Cyclopentyl | Cl | N | | |
| 243 | 2-Thienyl | Cyclohexyl | Cl | N | | |
| 244 | 3-Thienyl | CH₃ | Cl | N | | |
| 245 | 3-Thienyl | CH₃ | —O—C₆H₄—Cl (4-) | N | | |
| 246 | 3-Thienyl | C₂H₅ | Cl | N | 2970, 1506, 1275, 1135, 778, 702 | D₁:D₂ = 2:1 |
| 247 | 3-Thienyl | C₂H₅ | Cl | CH | 86–88° C. | D₁:D₂ = 2:1 |
| 248 | 3-Thienyl | C₂H₅ | OCH₃ | N | | |
| 249 | 3-Thienyl | C₂H₅ | —O—C₆H₄—Cl (4-) | N | | |
| 250 | 3-Thienyl | C₂H₅ | —O—C₆H₄—F (4-) | N | | |
| 251 | 3-Thienyl | C₂H₅ | SC₆H₅ | N | 1502, 1439, 1274, 1137, 1011, 702 | D₁:D₂ = 2:1 |
| 252 | 3-Thienyl | C₂H₅ | SC₆H₅ | CH | 1501, 1476, 1274, 1136, 1095, 1013 | D₁:D₂ = 2:1 |

TABLE -continued $$\text{structure with X, N, D, A, R}^1$$

| Example | A | R¹ | D | X | m.p./IR[cm⁻¹] | Isomer |
|---|---|---|---|---|---|---|
| 253 | 3-Thienyl | $C_2H_5$ | S-C₆H₄-4-Cl | N | | |
| 254 | 3-Thienyl | $C_3H_7$ | Cl | N | | |
| 255 | 3-Thienyl | $C_3H_7$ | $OCH_3$ | N | | |
| 256 | 3-Thienyl | $C_3H_7$ | O-C₆H₄-4-Cl | N | | |
| 257 | 3-Thienyl | $C_3H_7$ | $SC_6H_5$ | N | | |
| 258 | 3-Thienyl | $C_3H_7$ | S-C₆H₄-4-Cl | N | | |
| 259 | 3-Thienyl | $C_6H_5$ | Cl | N | | |
| 260 | 3-Thienyl | $4\text{-Cl}-C_6H_4$ | Cl | N | | |
| 261 | 3-Thienyl | $2\text{-Cl}-C_6H_4$ | Cl | N | | |
| 262 | 3-Thienyl | $2,4\text{-Cl}_2-C_6H_3$ | Cl | N | | |
| 263 | 3-Thienyl | $4\text{-F}-C_6H_4$ | Cl | N | | |
| 264 | 3-Thienyl | $4\text{-CH}_3-C_6H_4$ | Cl | N | | |
| 265 | 3-Thienyl | $4\text{-OCH}_3-C_6H_4$ | Cl | N | | |
| 266 | 2-Furyl | $CH_3$ | Cl | N | | |
| 267 | 2-Furyl | $C_2H_5$ | Cl | N | | |
| 268 | 2-Furyl | $C_2H_5$ | Cl | CH | | |
| 269 | 2-Furyl | $C_2H_5$ | $OCH_3$ | N | | |
| 270 | 2-Furyl | $C_3H_7$ | Cl | N | | |
| 271 | 2-Furyl | $C_3H_7$ | $OCH_3$ | N | | |
| 272 | 2-Furyl | $C_3H_7$ | O-C₆H₄-4-Cl | N | | |
| 273 | 2-Furyl | $C_3H_7$ | $SC_6H_5$ | N | | |
| 274 | 2-Furyl | $C_6H_{11}{}^3$ | Cl | N | 2927, 1489, 1227, 1150, 1076, 733 | $D_1:D_2 = 1:1$ |
| 275 | 2-Furyl | $C_6H_{11}{}^3$ | Cl | CH | 2928, 1505, 1275, 1135, 1011, 734 | $D_1:D_2 = 2:1$ |
| 276 | 2-Furyl | $C_6H_{11}{}^3$ | $OCH_3$ | N | | |
| 277 | 2-Furyl | $C_6H_{11}{}^3$ | O-C₆H₄-4-Cl | N | | |
| 278 | 2-Furyl | $C_6H_{11}{}^3$ | $SC_6H_5$ | N | | |
| 279 | 2-Furyl | $C_6H_5$ | Cl | N | | |
| 280 | 2-Furyl | $4\text{-Cl}-C_6H_4$ | Cl | N | | |
| 281 | 2-Furyl | $2\text{-Cl}-C_6H_4$ | Cl | N | | |
| 282 | 2-Furyl | $4\text{-F}-C_6H_4$ | Cl | N | | |
| 283 | 2-Furyl | $2\text{-F}-C_6H_4$ | Cl | N | | |
| 284 | 2-Furyl | $4\text{-Br}-C_6H_4$ | Cl | N | | |
| 285 | 2-Furyl | $4\text{-CH}_3-C_6H_4$ | Cl | N | | |
| 286 | 2-Furyl | $4\text{-OCH}_3-C_6H_4$ | Cl | N | | |
| 287 | 2-Pyridyl | $CH_3$ | Cl | N | | |
| 288 | 2-Pyridyl | $C_2H_5$ | Cl | N | | |
| 289 | 2-Pyridyl | $C_2H_5$ | Cl | CH | | |
| 290 | 2-Pyridyl | $C_2H_5$ | $OCH_3$ | N | | |

TABLE -continued

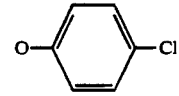

| Example | A | R¹ | D | X | m.p./IR[cm⁻¹] | Isomer |
|---|---|---|---|---|---|---|
| 291 | 2-Pyridyl | $C_2H_5$ | 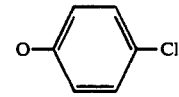 | N | | |
| 292 | 2-Pyridyl | $C_3H_7$ | Cl | N | | |
| 293 | 2-Pyridyl | $C_3H_7$ | Cl | CH | | |
| 294 | 2-Pyridyl | $C_3H_7$ | $OCH_3$ | N | | |
| 295 | 2-Pyridyl | $C_3H_7$ | 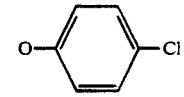 | N | | |
| 296 | 2-Pyridyl | $C_6H_5$ | Cl | N | | |
| 297 | 2-Pyridyl | $4\text{-Cl}-C_6H_4$ | Cl | N | | |
| 298 | 2-Pyridyl | $2\text{-Cl}-C_6H_4$ | Cl | N | | |
| 299 | 2-Pyridyl | $2\text{-F}-C_6H_4$ | Cl | N | | |
| 300 | 2-Pyridyl | $4\text{-F}-C_6H_4$ | Cl | N | | |
| 301 | 2-Pyridyl | $4\text{-Br}-C_6H_4$ | Cl | N | | |
| 302 | 2-Pyridyl | $4\text{-CH}_3-C_6H_4$ | Cl | N | | |
| 303 | 2-Pyridyl | $4\text{-OCH}_3-C_6H_4$ | Cl | N | | |
| 304 | 3-Pyridyl | $CH_3$ | Cl | N | | |
| 305 | 3-Pyridyl | $CH_3$ | Cl | N | | |
| 306 | 3-Pyridyl | $C_2H_5$ | Cl | N | | |
| 307 | 3-Pyridyl | $C_2H_5$ | Cl | CH | | |
| 308 | 3-Pyridyl | $C_2H_5$ | $OCH_3$ | N | | |
| 309 | 3-Pyridyl | $C_2H_5$ | 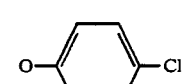 | N | | |
| 310 | 3-Pyridyl | $C_2H_5$ | $SC_6H_5$ | N | | |
| 311 | 3-Pyridyl | $C_3H_7$ | Cl | N | | |
| 312 | 3-Pyridyl | $C_3H_7$ | Cl | CH | | |
| 313 | 3-Pyridyl | $C_3H_7$ | $OCH_3$ | N | | |
| 314 | 3-Pyridyl | $C_3H_7$ | 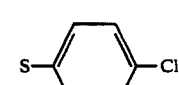 | N | | |
| 315 | 3-Pyridyl | $C_3H_7$ | 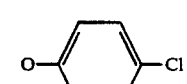 | N | | |
| 316 | 3-Pyridyl | $C_6H_5$ | Cl | N | | |
| 317 | 3-Pyridyl | $4\text{-Cl}-C_6H_4$ | Cl | N | | |
| 318 | 3-Pyridyl | $2\text{-Cl}-C_6H_4$ | Cl | N | | |
| 319 | 3-Pyridyl | $4\text{-F}-C_6H_4$ | Cl | N | | |
| 320 | 3-Pyridyl | $2\text{-F}-C_6H_4$ | Cl | N | | |
| 321 | 3-Pyridyl | $4\text{-Br}-C_6H_4$ | Cl | N | | |
| 322 | 3-Pyridyl | $4\text{-CH}_3-C_6H_4$ | Cl | N | | |
| 323 | 3-Pyridyl | $4\text{-OCH}_3-C_6H_4$ | Cl | N | | |
| 324 | 4-Pyridyl | $CH_3$ | Cl | N | | |
| 325 | 4-Pyridyl | $CH_3$ | Cl | CH | | |
| 326 | 4-Pyridyl | $C_2H_5$ | Cl | N | | |
| 327 | 4-Pyridyl | $C_2H_5$ | Cl | CH | | |
| 328 | 4-Pyridyl | $C_2H_5$ | $OCH_3$ | N | | |
| 329 | 4-Pyridyl | $C_2H_5$ |  | N | | |

TABLE -continued $$\begin{array}{c} X \\ \| \\ N \diagdown \diagup N \diagdown \overset{D}{\underset{A}{\overset{|}{C}}} \\ \underset{A}{\overset{|}{C}} - R^1 \end{array}$$

| Example | A | $R^1$ | D | X | m.p./IR[cm$^{-1}$] | Isomer |
|---|---|---|---|---|---|---|
| 330 | 4-Pyridyl | $C_2H_5$ | $SC_6H_5$ | N | | |
| 331 | 4-Pyridyl | $C_3H_7$ | Cl | N | | |
| 332 | 4-Pyridyl | $C_3H_7$ | Cl | CH | | |
| 333 | 4-Pyridyl | $C_3H_7$ | $OCH_3$ | N | | |
| 334 | 4-Pyridyl | $C_3H_7$ | O—C$_6$H$_4$—Cl | N | | |
| 335 | 4-Pyridyl | $C_3H_7$ | $SC_6H_5$ | N | | |
| 336 | 4-Pyridyl | $C_6H_5$ | Cl | N | | |
| 337 | 4-Pyridyl | 4-Cl—$C_6H_4$ | Cl | N | | |
| 338 | 4-Pyridyl | 2-Cl—$C_6H_4$ | Cl | N | | |
| 339 | 4-Pyridyl | 4-F—$C_6H_4$ | Cl | N | | |
| 340 | 4-Pyridyl | 2-F—$C_6H_4$ | Cl | N | | |
| 341 | 4-Pyridyl | 4-Br—$C_6H_4$ | Cl | N | | |
| 342 | 4-Pyridyl | 4-CH$_3$—$C_6H_4$ | Cl | N | | |
| 343 | 4-Pyridyl | 4-OCH$_3$—$C_6H_4$ | Cl | N | | |
| 344 | 4-Oxazolyl | $CH_3$ | Cl | N | | |
| 345 | 4-Oxazolyl | $C_2H_5$ | Cl | N | | |
| 346 | 5-Oxazolyl | $CH_3$ | Cl | N | | |
| 347 | 5-Oxazolyl | $C_2H_5$ | Cl | N | | |
| 348 | 5-Oxazolyl | $C_6H_5$ | Cl | N | | |
| 349 | 3-Isoxazolyl | $CH_3$ | Cl | N | | |
| 350 | 3-Isoxazolyl | $C_2H_5$ | Cl | N | | |
| 351 | 3-Isoxazolyl | $C_6H_5$ | Cl | N | | |
| 352 | 4-Isoxazolyl | $CH_3$ | Cl | N | | |
| 353 | 4-Isoxazolyl | $C_2H_5$ | Cl | N | | |
| 354 | 4-Isoxazolyl | $C_6H_5$ | Cl | N | | |
| 355 | 5-Isoxazolyl | $CH_3$ | Cl | N | | |
| 356 | 5-Isoxazolyl | $C_2H_5$ | Cl | N | | |
| 357 | 5-Isoxazolyl | $C_6H_5$ | Cl | N | | |
| 358 | 4-Thiazolyl | $CH_3$ | Cl | N | | |
| 359 | 4-Thiazolyl | $C_2H_5$ | Cl | N | | |
| 360 | 4-Thiazolyl | $C_6H_5$ | Cl | N | | |
| 361 | 5-Thiazolyl | $CH_3$ | Cl | N | | |
| 362 | 5-Thiazolyl | $C_2H_5$ | Cl | N | | |
| 363 | 5-Thiazolyl | $C_6H_5$ | Cl | N | | |
| 364 | (dioxolanyl) | $CH_3$ | Cl | N | | |
| 365 | (dioxolanyl) | $C_6H_5$ | Cl | N | | |
| 366 | $CH_2CH_2CO_2CH_3$ | $C_6H_5$ | Cl | N | 1729, 1506, 1276, 1202, 1135, 702 cm−1 | $D_1:D_2 = 3:1$ |
| 367 | $CH_2CH_2CO_2CH_3$ | $C_6H_5$ | Cl | CH | | |
| 368 | $CH_2CH_2CO_2CH_3$ | $C_6H_5$ | $OCH_3$ | N | | |
| 369 | $CH_2CH_2CO_2CH_3$ | $C_6H_5$ | $SC_6H_5$ | N | | |
| 370 | $CH_3$ | O—C$_6$H$_4$—C$_6$H$_4$— | Cl | N | resin | $D_1:D_2 = 3:1$ |

$D_1:D_2$ = ratio of the diastereomers formed

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

Erysiphe graminis in cereals, *Erysiphe cichoracearum* and *Sphaerotheca fuliginea* in cucurbits, *Podosphaera leucotricha* in apples, *Uncinula necator* in vines, *Puccinia species* in cereals, *Rhizoctonia solani* in cotton, *Ustilago species* in cereals and sugar cane, *Venturia inaequalis* (scab) in apples, Helminthosporium species in cereals, *Septoria nodorum* in wheat, *Botrytis cinerea* (gray mold) in strawberries and grapes, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in various plants, *Plasmopara viticola* in grapes, Alternaria species in fruit and vegetables.

The compounds are applied by spraying or dusting the plants with the active ingredients, or treating the seeds of the plants with the active ingredients. They may be applied before or after infection of the plants or seeds by the fungi. Either the fungi themselves, the soil, or the plants, seed or materials to be protected from fungus attack, are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins, (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

The fungicides generally contain from 0.1 to 95, and preferably from 0.5 to 90, wt. % of active ingredient. The application rates are from 0.02 to 3 kg or more of active ingredient per hectare, depending on the type of effect desired. The novel compounds may also be used for protecting materials (timber),, e.g., on Paecilomyces variotii. When the active ingredients are used for treating seed, amounts of from 0.001 to 50, and preferably from 0.01 to 10, g per kg of seed are generally required.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 9 and 10 parts by weight of N-methyl-α-pyrrolidone, which is suitable for application in the form of very fine drops.

II. A mixture of 20 parts by weight of compound no. 16, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 80, 40 parts by weight of cyclohexanone, 30 parts by weight of isobutanol, 20 parts by weight of the adduct of 40 moles of ethylene oxide and 1 mole of castor oil. By finely distributing the solution in water an aqueous dispersion is obtained.

IV. An aqueous disperson of 20 parts by weight of compound no. 225, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By finely distributing the solution in water an aqueous dispersion is obtained.

V. A hammer-milled mixture of 80 parts by weight of compound no. 226, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 246 and 97 parts by weight of particulate kaolin. The dust conatins 3 wt. % of the active ingredient.

VII. An intimate mixture of 30 parts by weight of compound no. 247, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 251, 10 parts of the sodium salt of a phenosulfonic acid-urea-formaldehyde condensate, 2 parts of silica gel and 48 parts of water, which dispersion can be further diluted.

IX. A stable oily dispersion of 20 parts by weight of compound no. 252, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

USE EXAMPLES

The active ingredients used for comparison purposes were 1-(1,2,4-triazol-1yl)-1-phenylthio-2-methyl-2-phenylpropane (A) disclosed in EP 91,219,1-(1,2,4-triazol-1-yl)-1-(4-chlorophenylthio)-2-methyl-2-phenylpropane (B) disclosed in EP 91,219 and 1-methoxy-1-(1,2,4-triazol-1-yl)-2-phenylethane (C) disclosed in DE 2,640,823.

USE EXAMPLE 1

Action on wheat brown rust

Leaves of pot-grown wheat seedlings of the "Kanzler" variety were dusted with spores of brown rust (*Puccinia recondita*). The post were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. Aftr the sprayed-on layer had dried, the plants were set up in the greenhouse at 20° to 22° C. and a relative humidity of 65 to 70%. The extent of rust fungus spread on the leaves was assessed after 8 days.

The results show that active ingredients 2, 80 and 247, applied as 0.025 wt. % spray liquors, have a better fungicidal action (90%) than prior art comparative compounds A, B and C (40%).

USE EXAMPLE 2

Action on *Botrytis cinerea*

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprayed with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves. Leaf attack was assessed.

The results show that active ingredients 225 and 247, applied as 0.05 wt. % spray liquors, have a better fungicidal action (85%) than prior art comparative compounds A, B and C (10%).

USE EXAMPLE 3

Action on *Pyrenophora teres*

Barley seedlings of the "Igri" variety were sprayed to runoff at the 2-leaf stage with aqueous suspensions containing (dry basis) 80% of active ingredient and 20% emulsifier. After 24 hours the plants were inoculated with a spore suspension of the fungus Pyrenophora teres and placed for 48 hours in a high-humidity climatic cabinet kept at 18° C. The plants were then cultivated for a further 5 days in the greenhouse at 20°–22° C. and a relative humidity of 70%. The extent of fungus spread was then determined.

The results show that active ingredients 9, 16, 80, 225, 226, 246, 247, 251 and 252, applied as 0.05wt. % spray liquors, have a better fungicidal action (95%) than prior art comparative compounds A, B and C (30%).

We claim:

1. A compound of the formula I

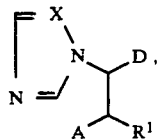

where
A and $R^1$ are identical or different and are each $C_1$-$C_8$-alkyl, phenyl, biphenyl, naphthyl, benzyl, $C_3$-$C_6$-cycloalkyl, $C_1$-$C_8$-alkoxy, $C_1$-$C_8$-alkylthio, phenoxy, benzyloxy, phenylthio, methoxycarbonylethyl, furyl or thienyl, and these radicals may be monosubstituted to trisubstituted by halogen, nitro, phenoxy, $C_1$-$C_4$-alkyl, $C_1$-$C_4$-alkoxy or $C_1$-$C_4$-haloalkyl, with the proviso that at least one of the substituents A and $R^1$ is furyl or thienyl, each of which is unsubstituted or mono- to trisubstituted by halogen, nitro, phenoxy, $C_1$-$C_4$-alkyl, $C_1$-$C_4$-alkoxy or $C_1$-$C_4$-haloalkyl, D is halogen, and X is N, or its plant-tolerated acid addition salts or metal complex compounds.

2. A fungicidal composition comprising an inert carrier and a fungicidally effective amount of an azolylethane derivative of the formula I

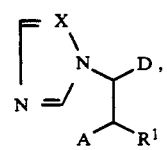

where
A and $R^1$ are identical or different and are each $C_1$-$C_8$-alkyl, phenyl, biphenyl, naphthyl, benzyl, $C_3$-$C_6$-cycloalkyl, $C_1$-$C_8$-alkoxy, $C_1$-$C_8$-alkylthio, phenoxy, benzyloxy, phenylthio, methoxycarbonylethyl, furyl or thienyl, and these radicals may be monosubstituted to trisubstituted by halogen, nitro, phenoxy, $C_1$-$C_4$-alkyl, $C_1$-$C_4$-alkoxy or $C_1$-$C_4$-haloalkyl, with the proviso that at least one of the substituents A and $R^1$ is furyl or thienyl, each of which is unsubstituted or mono- to trisubstituted by halogen, nitro, phenoxy, $C_1$-$C_4$-alkyl, $C_1$-$C_4$-alkoxy or $C_1$-$C_4$-haloalkyl, D is halogen, and X is N, or a plant-tolerated acid addition salt or metal complex thereof.

3. A process for combating fungi, wherein a fungicidally effective amount of an azolylethane derivative of the formula I

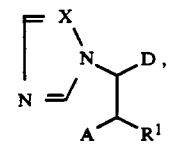

where
A and $R^1$ are identical or different and are each $C_1$-$C_8$-alkyl, phenyl, biphenyl, naphthyl, benzyl, $C_3$-$C_6$-cycloalkyl, $C_1$-$C_8$-alkoxy, $C_1$-$C_8$-alkylthio, phenoxy, benzyloxy, phenylthio, methoxycarbonylethyl, furyl or thienyl, and these radicals may be monosubstituted to trisubstituted by halogen, nitro, phenoxy, $C_1$-$C_4$-alkyl, $C_1$-$C_4$-alkoxy or $C_1$-$C_4$-haloalkyl, with the proviso that at least one of the substituents A and $R^1$ is furyl or thienyl, each of which is unsubstituted or mono- to trisubstituted by halogen, nitro, phenoxy, $C_1$–$C_4$-alkyl, $C_1$–$C_4$-alkoxy or $C_1$–$C_4$-haloalkyl, D is halogen, and X is N, or its plant-tolerated acid addition salt or metal complex thereof, is allowed to act on fungi, or plants, or plant habitat, plant materials, timber or seed threatened by fungus attack.

4. A compound of claim 1 wherein A is 2-thienyl, $R^1$ is propyl, and D is chloro.

5. A compound according to claim 1 wherein A is 3-thienyl, $R^1$ is ethyl, and D is chloro.

6. A compound according to claim 1 wherein A is 2-furyl, $R^1$ is hexyl, and D is chloro.

* * * * *